United States Patent
Baxter et al.

(10) Patent No.: US 11,794,127 B2
(45) Date of Patent: Oct. 24, 2023

(54) METHODS AND SYSTEMS FOR SEPARATING COMPOUNDS

(71) Applicant: Sustainable Energy Solutions, Inc., Provo, UT (US)

(72) Inventors: Larry Baxter, Orem, UT (US); Stephanie Burt, Provo, UT (US); Dave Frankman, Provo, UT (US); Christopher Hoeger, Provo, UT (US); Eric Mansfield, Spanish Fork, UT (US); Skyler Chamberlain, Provo, UT (US); Kyler Stitt, Lindon, UT (US)

(73) Assignee: Sustainable Energy Solutions, Inc, Orem, UT (US)

(*) Notice: Subject to any disclaimer, the term of this patent is extended or adjusted under 35 U.S.C. 154(b) by 493 days.

(21) Appl. No.: 16/834,927

(22) Filed: Mar. 30, 2020

(65) Prior Publication Data

US 2021/0299591 A1   Sep. 30, 2021

(51) Int. Cl.
*F25J 3/02* (2006.01)
*B01D 7/02* (2006.01)
(Continued)

(52) U.S. Cl.
CPC .............. *B01D 7/02* (2013.01); *F25J 3/0266* (2013.01); *F25J 3/067* (2013.01); *F25J 3/08* (2013.01);
(Continued)

(58) Field of Classification Search
CPC .......... F25J 3/08; F25J 3/0266; F25J 2210/80; F25J 2205/20; F25J 2205/067; B01D 7/02
See application file for complete search history.

(56) References Cited

U.S. PATENT DOCUMENTS 6,053,007 A * 4/2000 Victory ................. F25J 3/0247
                                                        62/619
2010/0147022 A1  6/2010 Hart et al.
(Continued)

FOREIGN PATENT DOCUMENTS

WO    2011046658 A1   4/2011

OTHER PUBLICATIONS

International Search Report and Written Opinion for International Application No. PCT/US2021/024292, dated Jul. 15, 2021.

*Primary Examiner* — Brian M King
(74) *Attorney, Agent, or Firm* — Cook Alex Ltd.

(57) ABSTRACT

Methods and systems for separating a desublimatable compound from hydrocarbons is disclosed. A feed fluid stream, consisting of a hydrocarbon and a desublimatable compound, is passed into an upper chamber of a vessel. The feed fluid stream is cooled in the upper chamber, thereby desublimating a portion of the desublimatable compound out of the feed liquid stream to form a product gas stream and a desublimatable compound snow which is collected in the lower chamber of the vessel. A lower portion of the desublimatable compound snow is melted to form a liquid desublimatable compound stream such that an upper portion of the solid desublimatable compound snow remains as an insulative barrier between the upper chamber and the liquid desublimatable compound stream. The liquid desublimatable compound stream is removed at a rate that matches a production rate of the solid desublimatable compound snow, thereby maintaining the insulative barrier.

20 Claims, 2 Drawing Sheets

(51) Int. Cl.
   *F25J 3/08* (2006.01)
   *F25J 3/06* (2006.01)
   *C07C 51/573* (2006.01)
(52) U.S. Cl.
   CPC ........ *B01D 2256/24* (2013.01); *C07C 51/573* (2013.01); *F25J 2205/20* (2013.01)

(56) References Cited

U.S. PATENT DOCUMENTS

| | | |
|---|---|---|
| 2010/0281916 A1 | 11/2010 | Van Der Vaart |
| 2012/0137726 A1* | 6/2012 | Currence ............... F25J 3/0238 62/611 |
| 2015/0159943 A1* | 6/2015 | Valencia ................ F25J 1/0022 62/625 |
| 2018/0209729 A1* | 7/2018 | Baxter ................. B01D 53/002 |
| 2020/0378681 A1* | 12/2020 | Du ....................... B01J 20/3458 |

* cited by examiner

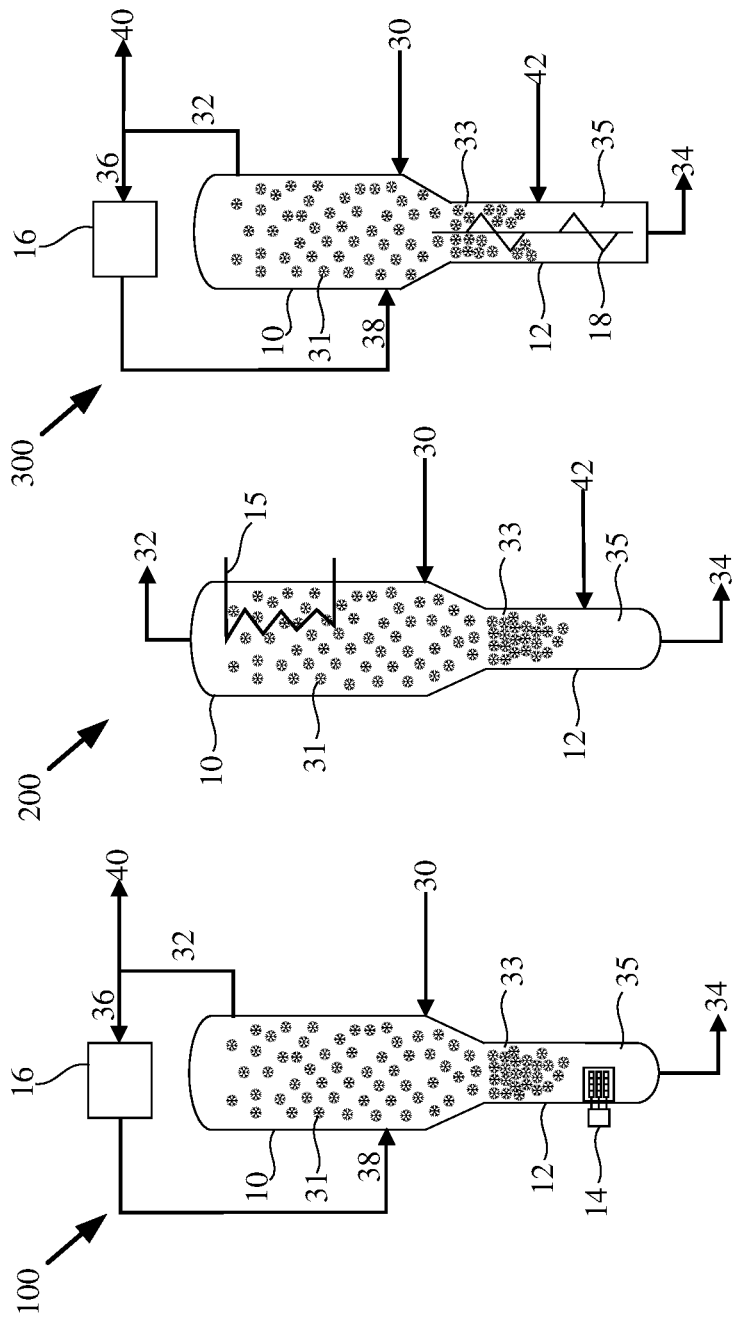

METHODS AND SYSTEMS FOR
SEPARATING COMPOUNDS

TECHNICAL FIELD

The methods and processes described herein relate generally to fluid separations.

BACKGROUND

Separation of fluid components is often energy intensive or complex. Separating components can be done, but the higher the purity required, the more unit operations are typically required. Alternatives to traditional fluid separation techniques are required.

SUMMARY

In a first aspect, the disclosure provides a method for continuously separating a desublimatable compound from hydrocarbons. A vessel with an upper chamber and a lower chamber is provided. A feed fluid stream is passed into the upper chamber. The feed fluid stream consists of a hydrocarbon and a desublimatable compound. The feed fluid stream is cooled in the upper chamber, thereby desublimating a portion of the desublimatable compound out of the feed liquid stream to form a solid desublimatable compound snow and a product gas stream. The solid desublimatable compound snow is collected in the lower chamber. A lower portion of the solid desublimatable compound snow is melted to form a liquid desublimatable compound stream such that an upper portion of the solid desublimatable compound snow remains as an insulative barrier between the upper chamber and the liquid desublimatable compound stream. The liquid desublimatable compound stream is removed at a rate that matches a production rate of the solid desublimatable compound snow, thereby maintaining the insulative barrier. The product gas stream is removed from the upper chamber.

In a second aspect, the disclosure provides a method for continuously separating components. A vessel with an upper chamber and a lower chamber is provided. A feed fluid stream is passed into the upper chamber. The feed fluid stream consists of methane and carbon dioxide. A cold liquid stream is flashed into the upper chamber, thereby reducing the temperature of the upper chamber. The cold liquid stream consists of methane. The carbon dioxide is desublimated out of the feed fluid stream to form a solid carbon dioxide snow and a product gas stream. The solid carbon dioxide snow is collected in the lower chamber. A lower portion of the solid carbon dioxide snow is melted to form a liquid carbon dioxide stream such that an upper portion of the solid carbon dioxide snow remains as an insulative barrier between the upper chamber and the liquid carbon dioxide stream. The liquid carbon dioxide stream is removed at a rate that matches a production rate of the solid carbon dioxide snow, thereby maintaining the insulative barrier. The product gas stream is removed from the upper chamber.

In a third aspect, the disclosure provides a system for continuously separating components. A vessel consists of an upper chamber and a lower chamber. The upper chamber consists of a feed gas inlet, a cooling source, and a product gas outlet. The lower chamber consists of a product liquid outlet and a heat source. The feed fluid inlet is configured to pass a feed gas stream through the feed gas inlet into the upper chamber. The feed fluid stream consists of a hydrocarbon and a desublimatable compound. The cooling source cools the feed gas stream, thereby desublimating a portion of the desublimatable compound out of the feed gas stream to form a solid desublimatable snow and a product gas stream. The solid desublimatable compound snow falls into the lower chamber. A heat source melts a lower portion of the solid desublimatable compound snow in the lower chamber to form a liquid desublimatable compound stream such that an upper portion of the solid desublimatable compound snow remains as an insulative barrier between the upper chamber and the liquid desublimatable compound stream. The product liquid outlet is configured to remove the liquid desublimatable compound stream at a rate that matches a production rate of the solid desublimatable compound snow, thereby maintaining the insulative barrier. The product gas outlet is configured to remove the product gas stream from the upper chamber.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

FIG. 1 is a flow diagram showing a method for separating compounds.

FIG. 2 is a flow diagram showing a method for separating compounds.

FIG. 3 is a flow diagram showing a method for separating compounds.

DETAILED DESCRIPTION

Figure 4:
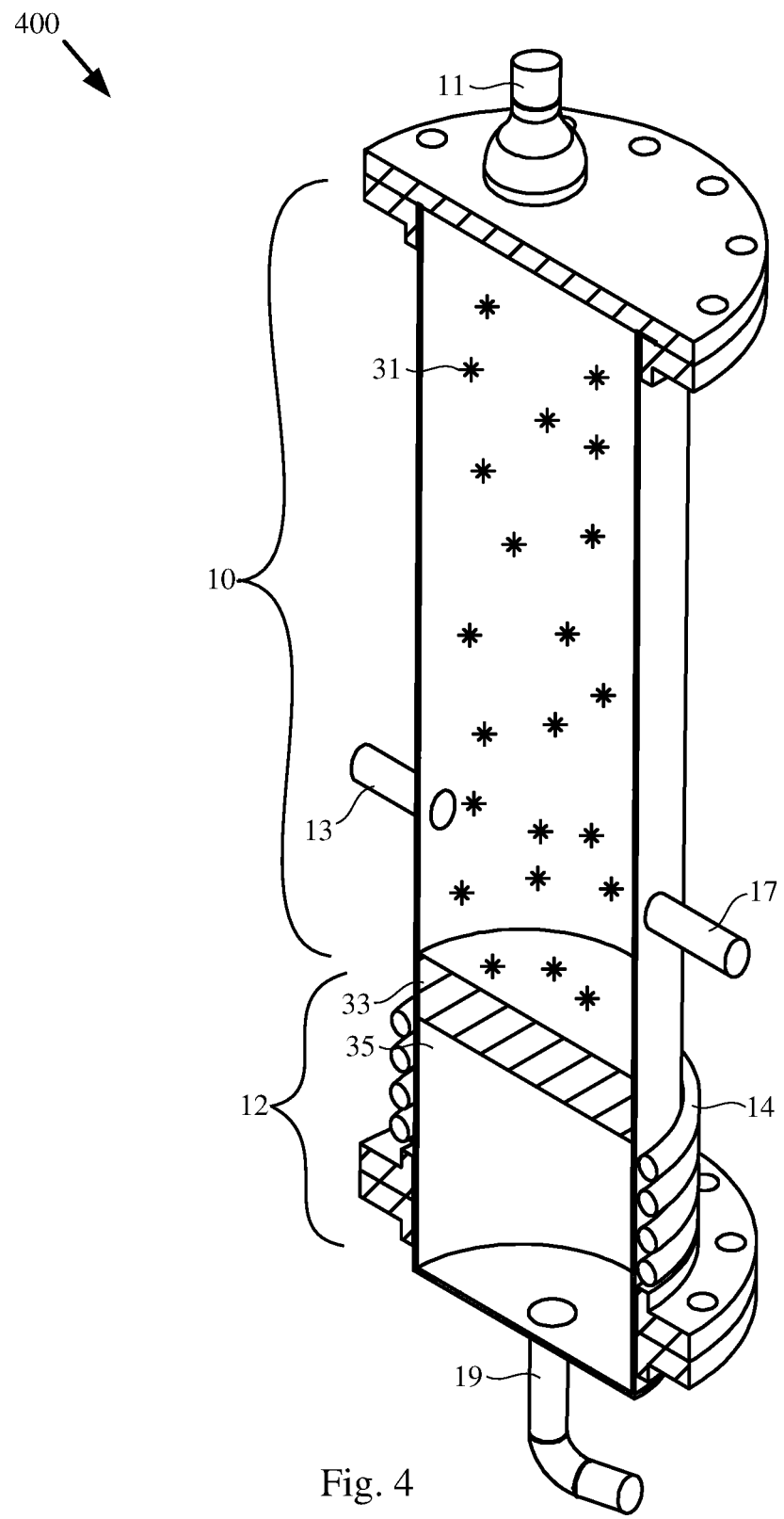
FIG. 4 is an isometric cutaway view of a system for separating compounds.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "C1" refers to methane, "C2" refers to ethane, "C3" refers to propane, and "C3+" hydrocarbons refers to hydrocarbons with three or more carbon atoms.

As used herein, "natural gas" refers to a gas containing primarily methane, and that may have other ingredients, such as ethane, propane, butane, water, and carbon dioxide.

As used herein, "desublimate" refers to a compound undergoing a phase change from gas directly to solid. "Desublimatable" means that at the pressure and temperature conditions in a vessel, the compound is able to desublimate. In a preferred embodiment, "desublimatable compounds" include carbon dioxide, sulfur oxides, nitrogen oxides, carbon monoxide, and combinations thereof.

Separations of components is often complicated by the presence of components that are miscible or have similar boiling points. For example, propane has some solubility in water and heptane has a boiling point nearly identical to water. Streams of hydrocarbons contaminated with carbon dioxide and water add to the overall complications. The present invention discloses methods and systems for separating desublimatable compounds, such as carbon dioxide, from hydrocarbons, such as natural gas. In one embodiment of the present invention, a feed liquid or gas stream containing a hydrocarbon and a desublimatable compound is passed into an upper chamber of a vessel. In the instance that the feed stream is a liquid, passing the feed stream into the upper chamber flashes the stream to a gas. A second stream, primarily composed of the hydrocarbon, is flashed into the vessel. The flashing of one or both streams cools the upper chamber such that the desublimatable compound is cooled and desublimates directly to a solid snow. This solid snow collects in a lower chamber of the vessel where it is melted. The melting, by heating element or reinjection of a heated liquid desublimatable compound stream, occurs in a bottom portion of the lower chamber. The snow is melted at a rate that an upper portion of the solid snow remains as a solid, providing an insulative barrier between the upper chamber and the resultant liquid. The liquid is removed at a rate to maintain the insulative barrier, as well. The gas formed in the upper chamber is also removed from the vessel. By this process, a compound, such as carbon dioxide, can be removed from hydrocarbons, such as natural gas, in a single vessel. This eliminates any solids handling issues. Further, as the compound snow descends and is melted from solid to liquid, any hydrocarbons trapped in void spaces of the snow are expelled as the void spaces collapse, driving the hydrocarbons out of the resultant liquid and up into the upper chamber, increasing separation purity.

Now referring to FIG. 1, FIG. 1 is a flow diagram showing a method for separating compounds that may be used in one embodiment of the present invention. A vessel 100 consists of an upper chamber 10 and a lower chamber 12. An inductive heater 14 is installed in a lower portion of the lower chamber 12. The upper chamber is kept at a pressure of 6 bar. A feed fluid stream 30 is a natural gas stream and contains at least 20 wt % carbon dioxide. The feed fluid stream 30 is at a pressure of at least 25 bar and a temperature less than −55° C. A cold liquid stream 38, a natural gas stream with no more than 3 wt % carbon dioxide, is at a pressure of 50 bar and a temperature less than −102° C. In other words, the cold liquid stream 38 meets standards for pipeline transportation of natural gas. The feed fluid stream 30 is passed into the upper chamber 10 where any liquid present in the feed fluid stream 30 is flashed to a vapor. Simultaneously, the cold liquid stream 38 is flashed into the upper chamber 10, resulting in further vapor. The vaporization requires heat which is absorbed from the vapor and results in the carbon dioxide desublimating to form a solid carbon dioxide snow 31 in the upper chamber 10. This solid carbon dioxide snow 31 falls from the upper chamber 10 into a top portion 33 of the lower chamber 12.

The inductive heater 14 warms a lower portion 35 of the lower chamber 12. This melts the solid carbon dioxide snow located in the lower portion 35, forming a liquid carbon dioxide stream 34. The heat is kept low enough to only melt the lower portion 35 while leaving the solid carbon dioxide snow settled in the upper portion 33 as an insulative barrier between the upper chamber 10 and the liquid carbon dioxide stream. The term "insulative" means first that the heat does not propagate back into the upper chamber 10 and second that the vapor of the upper chamber 10 is physically separated from the liquid carbon dioxide stream 34, preventing vaporization of the liquid back into the vapor. The liquid carbon dioxide stream 34 is removed at a rate that matches the production rate of the solid carbon dioxide snow 31, maintaining the insulative barrier in upper portion 33.

The vapor that did not desublimate leaves the upper chamber 10 as product gas stream 32. A portion of the product gas stream 36 is passed through a refrigeration loop 16 where the product gas stream is pressurized and cooled to produce the cold liquid stream 38. The balance of the product gas stream 40 is a product stream that can be further processed to remove the remaining carbon dioxide or can be used as a natural gas stream without further processing.

In this embodiment, if the surface area around the lower portion 35 is sufficient, the use of an inductive heater 14 may not be necessary. Simply removing any insulation from the lower portion of the lower chamber 12 may be able to provide sufficient heat from ambient air to melt the solid carbon dioxide snow.

Now referring to FIG. 2, FIG. 2 is a flow diagram showing a method for separating compounds that may be used in one embodiment of the present invention. A vessel 200 consists of an upper chamber 10 and a lower chamber 12. The upper chamber contains an indirect-contact heat exchanger 15 equipped with vibrators. A feed gas stream 30, consisting of a desublimatable compound and hydrocarbons, is passed into the upper chamber 10. The desublimatable compound desublimates onto the heat exchanger 15, which is vibrated to cause the solids to flake off as a solid desublimatable compound snow 31 which falls from the upper chamber 10 into a top portion 33 of the lower chamber 12.

A warm liquid stream 42, consisting of the desublimatable compound, is pumped into a lower portion 35 of the lower section 12, melting the solid desublimatable compound snow located in the lower portion 35, forming a liquid desublimatable compound stream 34. The temperature and flow rate of the warm liquid stream 42 is kept low enough to only melt the lower portion 35 while leaving the solid desublimatable compound snow settled in the upper portion 33 as an insulative barrier between the upper chamber 10 and the liquid desublimatable compound stream. The term "insulative" means first that the heat does not propagate back into the upper chamber 10 and second that the vapor of the upper chamber 10 is physically separated from the liquid desublimatable compound stream 34, preventing vaporization of the liquid back into the vapor. The liquid desublimatable compound stream 34 is removed at a rate that matches the production rate of the solid desublimatable compound snow 31, maintaining the insulative barrier in upper portion 33.

The vapor that did not desublimate leaves the upper chamber 10 as product gas stream 32. A portion of the product gas stream 36 is passed through a refrigeration loop 16 where the product gas stream is pressurized and cooled to produce the cold liquid stream 38. The balance of the product gas stream 40 is a product stream.

Now referring to FIG. 3, FIG. 3 is a flow diagram showing a method for separating compounds that may be used in one embodiment of the present invention. A vessel 300 consists of an upper chamber 10 and a lower chamber 12. An auger 18 is installed in the lower chamber 12. A feed fluid stream 30, consisting of a desublimatable compound and hydrocarbons, is passed into the upper chamber 10 where any liquid present in the feed fluid stream 30 is flashed to a vapor. Simultaneously, a cold liquid stream 38 is flashed into the upper chamber 10, resulting in further vapor. The vaporization requires heat which is absorbed from the vapor and results in the desublimatable compound desublimating to form a solid desublimatable compound snow 31 in the upper chamber 10. This solid desublimatable compound snow 31 falls from the upper chamber 10 into a top portion 33 of the lower chamber 12.

A warm liquid stream 42, consisting of the desublimatable compound, is pumped into a lower portion 35 of the lower section 12, melting the solid desublimatable compound snow located in the lower portion 35, forming a liquid desublimatable compound stream 34. The temperature and flow rate of the warm liquid stream 42 is kept low enough to only melt the lower portion 35 while leaving the solid desublimatable compound snow settled in the upper portion 33 as an insulative barrier between the upper chamber 10 and the liquid desublimatable compound stream. The term "insulative" means first that the heat does not propagate back into the upper chamber 10 and second that the vapor of the upper chamber 10 is physically separated from the liquid desublimatable compound stream 34, preventing vaporization of the liquid back into the vapor. The liquid desublimatable compound stream 34 is removed at a rate that matches the production rate of the solid desublimatable compound snow 31, maintaining the insulative barrier in upper portion 33. The solid desublimatable compound is conveyed from the upper portion 33 to the lower portion 35 by the auger 18.

The vapor that did not desublimate leaves the upper chamber 10 as product gas stream 32. A portion of the product gas stream 36 is passed through a refrigeration loop 16 where the product gas stream is pressurized and cooled to produce the cold liquid stream 38.

Now referring to FIG. 4, FIG. 4 is an isometric cutaway view of a system for separating compounds that may be used in one embodiment of the present invention. The vessel 400 consists of an upper chamber 10 and a lower chamber 12. The upper chamber has a feed gas inlet, a cooling source, and a product gas outlet. The lower chamber has a product liquid outlet and a heat source 14.

The feed fluid inlet is configured to pass a feed gas stream through the feed gas inlet into the upper chamber. The feed fluid stream consists of a hydrocarbon and a desublimatable compound. The cooling source cools the feed fluid stream. In this embodiment, the cooling source is a cold liquid stream that is flashed into the upper chamber 10. The vaporization requires heat which is absorbed from the feed fluid stream and results in the desublimatable compound desublimating to form a solid desublimatable compound snow in the upper chamber 10, as well as a product gas stream. The solid desublimatable compound snow falls into the lower chamber 12, forming an insulative barrier 33.

In this embodiment, the heat source 14 is a set of heating coils wrapped around a lower portion 35 of the lower chamber 12. The heat source 14 melts a lower portion of the solid desublimatable compound snow in the lower chamber to form a liquid desublimatable compound stream in a manner that an upper portion of the solid desublimatable compound snow remains as an insulative barrier between the upper chamber and the liquid desublimatable compound stream. The product liquid outlet is configured to remove the liquid desublimatable compound stream at a rate that matches a production rate of the solid desublimatable compound snow, thereby maintaining the insulative barrier. The product gas outlet is configured to remove the product gas stream from the upper chamber.

In some embodiments, the solid may bridge as it collects as insulative barrier 33. Heating the walls is not always necessary, but in some embodiments, heating will prevent bridging and lead to a proper insulative barrier 33.

In some embodiments, the desublimatable compound is selected from the group consisting of carbon dioxide, sulfur oxides, nitrogen oxides, carbon monoxide, and combinations thereof. In some embodiments, the hydrocarbon is selected from the group consisting of methane, ethane, propane, and combinations thereof.

The invention has been described with reference to various specific and preferred embodiments and techniques. Nevertheless, it is understood that many variations and modifications may be made while remaining within the spirit and scope of the invention.

What is claimed is:

1. A method for continuously separating a desublimatable compound from hydrocarbons comprising:
   providing a vessel comprising an upper chamber and a lower chamber;
   passing a feed fluid stream into the upper chamber, the feed fluid stream comprising a hydrocarbon and a desublimatable compound;
   cooling the feed fluid stream in the upper chamber, thereby desublimating a portion of the desublimatable compound out of the feed fluid stream to form a solid desublimatable compound snow and a product gas stream;
   collecting the solid desublimatable compound snow in the lower chamber;
   melting a lower portion of the solid desublimatable compound snow to form a liquid desublimatable compound stream such that an upper portion of the solid desublimatable compound snow remains as an insulative barrier that physically separates the upper chamber from all of the liquid desublimatable compound stream;
   removing the liquid desublimatable compound stream at a rate that matches a production rate of the solid desublimatable compound snow, thereby maintaining the insulative barrier; and
   removing the product gas stream from the upper chamber.

2. The method of claim 1, wherein the desublimatable compound is selected from the group consisting of carbon dioxide, sulfur oxides, nitrogen oxides, carbon monoxide, and combinations thereof.

3. The method of claim 1, wherein the hydrocarbon is selected from the group consisting of methane, ethane, propane, and combinations thereof.

4. The method of claim 1, wherein cooling the feed fluid stream comprises flashing a cold liquid stream into the upper chamber, thereby reducing the temperature of the upper chamber, the cold liquid stream comprising the hydrocarbon.

5. The method of claim 4, further comprising passing a portion of the product gas stream through a refrigeration loop to produce the cold liquid stream.

6. The method of claim 1, wherein melting comprises injecting a warm liquid desublimatable compound stream into the lower chamber.

7. The method of claim 1, wherein melting comprises heating the lower chamber with a heating element.

8. A method for continuously separating components comprising:
   providing a vessel comprising an upper chamber and a lower chamber;
   passing a feed fluid stream into the upper chamber, the feed fluid stream comprising methane and carbon dioxide;
   flashing a cold liquid stream into the upper chamber, thereby reducing the temperature of the upper chamber, wherein the cold liquid stream comprises methane;
   desublimating the carbon dioxide out of the feed fluid stream to form a solid carbon dioxide snow and a product gas stream;
   collecting the solid carbon dioxide snow in the lower chamber;
   melting a lower portion of the solid carbon dioxide snow to form a liquid carbon dioxide stream such that an upper portion of the solid carbon dioxide snow remains as an insulative barrier that physically separates the upper chamber from all of the liquid carbon dioxide stream;
   removing the liquid carbon dioxide stream at a rate that matches a production rate of the solid carbon dioxide snow, thereby maintaining the insulative barrier; and
   removing the product gas stream from the upper chamber.

9. The method of claim 8, wherein the feed fluid stream comprises at least 20 wt % carbon dioxide, is at least 25 bar, and is less than −55° C.

10. The method of claim 8, wherein the feed fluid stream comprises C2+ natural gas components.

11. The method of claim 8, wherein the cold liquid stream comprises no more than 3 wt % carbon dioxide, is at least 50 bar, and is less than −102° C.

12. The method of claim 8, further comprising passing a portion of the product gas stream through a refrigeration loop to produce the cold liquid stream.

13. The method of claim 8, wherein melting comprises injecting a warm liquid carbon dioxide stream into the lower chamber.

14. The method of claim 8, wherein melting comprises heating the lower chamber with a heating element.

15. A system for continuously separating components comprising:
   a vessel comprising an upper chamber and a lower chamber;
   the upper chamber comprising a feed gas inlet, a cooling source, and a product gas outlet;
   the lower chamber comprising a product liquid outlet and a heat source;
   the feed gas inlet passing a feed gas stream through the feed gas inlet into the upper chamber, the feed gas stream comprising a hydrocarbon and a desublimatable compound;
   wherein the cooling source cools the feed gas stream, thereby desublimating a portion of the desublimatable compound out of the feed gas stream to form a solid desublimatable compound snow and a product gas stream, the solid desublimatable compound snow falling into the lower chamber;
   wherein a heat source melts a lower portion of the solid desublimatable compound snow in the lower chamber to form a liquid desublimatable compound stream in a manner that an upper portion of the solid desublimatable compound snow remains as an insulative barrier that physically separates the upper chamber from all of the liquid desublimatable compound stream;
   the product liquid outlet configured to remove the liquid desublimatable compound stream at a rate that matches a production rate of the solid desublimatable compound snow, thereby maintaining the insulative barrier; and
   the product gas outlet configured to remove the product gas stream from the upper chamber.

16. The system of claim 15, further comprising a refrigerant loop configured to receive, cool, and compress a portion of the product gas stream to form a cold liquid stream and wherein the cooling source is a result of flashing the cold liquid stream into the upper chamber.

17. The system of claim 15, wherein the heat source an inductive resistance heater embedded in or attached to walls of the lower chamber.

18. The system of claim 15, wherein the heat source is an indirect-contact heat exchanger.

19. The system of claim 15, wherein the lower chamber comprises an auger configured to convey the solids towards the product liquid outlet as the solids melt.

20. The system of claim 15, wherein the desublimatable compound is selected from the group consisting of carbon dioxide, sulfur oxides, nitrogen oxides, carbon monoxide, and combinations thereof.

* * * * *